(12) United States Patent  
Thakkar et al.

(10) Patent No.: US 9,346,743 B2  
(45) Date of Patent: May 24, 2016

(54) PROCESSES FOR THE SYNTHESIS OF 2-AMINO-4,6-DIMETHOXYBENZAMIDE AND OTHER BENZAMIDE COMPOUNDS

(71) Applicant: ALBEMARLE CORPORATION, Baton Rouge, LA (US)

(72) Inventors: Amit Thakkar, Byron Center, MI (US); Andrew G. Zeiler, Kalamazoo, MI (US); Anthony F. Skufca, Zachary, LA (US); James J. Springer, Saugatuck, MI (US); Bryce Kelly Assink, Kalamazoo, MI (US); Mario E. Lozanov, Baton Rouge, LA (US)

(73) Assignee: Albemarle Corporation, Baton Rouge, LA (US)

( * ) Notice: Subject to any disclaimer, the term of this patent is extended or adjusted under 35 U.S.C. 154(b) by 373 days.

(21) Appl. No.: 14/237,600

(22) PCT Filed: Oct. 9, 2013

(86) PCT No.: PCT/US2013/063995  
§ 371 (c)(1),  
(2) Date: Feb. 7, 2014

(87) PCT Pub. No.: WO2014/062428  
PCT Pub. Date: Apr. 24, 2014

(65) Prior Publication Data  
US 2016/0102046 A1   Apr. 14, 2016

Related U.S. Application Data

(60) Provisional application No. 61/713,688, filed on Oct. 15, 2012, provisional application No. 61/863,193, filed on Aug. 7, 2013.

(51) Int. Cl.  
*C07C 231/06* (2006.01)  
*C07C 231/12* (2006.01)  
*C07C 253/14* (2006.01)

(52) U.S. Cl.  
CPC ............. *C07C 231/06* (2013.01); *C07C 231/12* (2013.01); *C07C 253/14* (2013.01)

(58) Field of Classification Search  
CPC .... C07C 231/06; C07C 231/12; C07C 253/14  
See application file for complete search history.

(56) References Cited

U.S. PATENT DOCUMENTS

| | | | |
|---|---|---|---|
| 3,966,965 | A | 6/1976 | Sellstedt |
| 4,137,325 | A | 1/1979 | Sellstedt |
| 2006/0229289 | A1 | 10/2006 | Zhu et al. |
| 2007/0112047 | A1 | 5/2007 | Penning et al. |
| 2007/0259937 | A1 | 11/2007 | Giranda et al. |
| 2008/0188467 | A1 | 8/2008 | Wong |

FOREIGN PATENT DOCUMENTS

| | | |
|---|---|---|
| WO | 2004014895 | 2/2004 |
| WO | 2006074223 | 7/2006 |
| WO | 2007041357 | 4/2007 |

OTHER PUBLICATIONS

Guagnano et al, J. Med. Chem., 54(20), 7066-83, 2011.*  
Wu et al, J. Med. Chem., 2004, 47(8), 1969-1986.*  
Roy et al, J. Org. Chem., 2006, 71(1), 382-385.*  
Duan, et al; "2-Phenylquinazolin-4(3H)-one, a Class of Potent PDE5 Inhibitors with High Selectivity Versus PDE6"; Bioorganic & Medicinal Chemistry Letters, 19 (2009), pp. 2777-2779.

* cited by examiner

*Primary Examiner* — Shailendra Kumar  
(74) *Attorney, Agent, or Firm* — Marcy M. Hoefling; James A. Jubinsky; Nathan C. Dunn

(57) ABSTRACT

This invention provides a method for the synthesis of a 2-amino-4,6-dimethoxybenzamide and other benzamides of Compound I: wherein $R^1$, $R^2$, $R^3$, and $R^4$ each independently represent a hydrogen, a $C_1$-$C_6$ alkyl, or a $C_1$-$C_6$ alkoxy; and wherein $R_6$ and $R_7$ each independently represent a hydrogen, a $C_1$-$C_6$ alkyl, a protecting group, or a directing group.

(Compound I)

39 Claims, 2 Drawing Sheets

PROCESSES FOR THE SYNTHESIS OF 2-AMINO-4,6-DIMETHOXYBENZAMIDE AND OTHER BENZAMIDE COMPOUNDS

This application is a 371 of PCT/US13/63995, filed Oct. 9, 2013, which claims benefit of 61/713,688, filed Oct. 15, 2012, and claims benefit of 61/863,193, filed Aug. 7, 2013.

TECHNICAL FIELD

This invention relates to processes for the synthesis of 2-amino-4,6-dimethoxybenzamide and other benzamide compounds.

BACKGROUND

Benzamide compounds are used as intermediates for the synthesis of many pharmaceutical therapeutic drugs. In particular, 2-amino-4,6-dimethoxybenzamide was reported as an intermediate in U.S. Pat. No. 3,966,965 for the synthesis of oxamic acid derivatives for prevention of hypersensitivity in allergic reactions. More recent patents describe this compound as a valuable intermediate en route to new cardiovascular agents (U.S. 2008/0188467 and WO2008/92231 to Resverlogix Corp.).

2-Amino-4,6-dimethoxybenzamide has been prepared from 4,6-dimethoxyisatoic anhydride. The 4,6-dimethoxyisatoic anhydride was, in turn, prepared by a reaction of 4,6-dimethoxyanthranilic acid with phosgene (U.S. Pat. No. 4,191,840 and Org. Synth. 1947, 27, 45). A different route converts 3,5-dimethoxyaniline to its hydrochloride salt, after which the salt is reacted with oxalyl chloride to give 4,6-dimethoxyisatin. The isatin is converted to the target compound via an unstable carboxyl intermediate by reaction with sodium hydroxide and hydrogen peroxide followed by an EDCI/HOBt-mediated coupling to produce 2-amino-4,6-dimethoxybenzamide (WO 2008/92231).

The known processes for the synthesis of benzamide compounds and its derivatives often involve unstable intermediates, inefficient processes, and in some cases, a large number of steps, which result in yields that are unacceptably low, and manufacturing costs that are unacceptably high, for commercial use. There is a need in the art for commercially feasible processes for making benzamide compounds and their derivatives.

THE INVENTION

This invention meets the above-identified needs by providing processes for producing at least one (Compound I)

wherein the process comprises:
(i) combining at least one (Compound II)

with at least one halogenating agent to produce at least one (Compound III)

(ii) combining the at least one Compound III with at least one cyanating agent to produce at least one (Compound IV)

and;
(iii) combining the at least one Compound IV with at least one hydrating agent and/or at least one hydrating catalyst to produce the at least one Compound I,
wherein $R^1$ and $R^5$ each independently represent a hydrogen, a $C_1$-$C_6$ alkyl, a hydroxy, or a $C_1$-$C_6$ alkoxy;
wherein $R^2$, $R^3$, and $R^4$ each independently represent a hydrogen, a $C_1$-$C_6$ alkyl, or a $C_1$-$C_6$ alkoxy;
wherein $R^6$ and $R^7$ each independently represent a hydrogen, a $C_1$-$C_6$ alkyl, a protecting group, or a directing group;
wherein X represents a halo moiety or a halo-like moiety;
wherein at least one of $R^1$ and $R^5$ represent a hydrogen; and provided that in Compound II, $R^7$ represents a protecting group or a directing group, and either
  (1) prior to step (ii), the at least one Compound III is combined with at least one deprotecting agent such that the protecting group or directing group represented by $R^7$ is replaced with a hydrogen or a $C_1$-$C_6$ alkyl, or
  (2) prior to step (iii), the at least one Compound IV is combined with at least one deprotecting agent such that the protecting group or directing group represented by $R^7$ is replaced with a hydrogen or a $C_1$-$C_6$ alkyl.

This invention also meets the above-identified needs by providing processes for producing at least one (Compound I)

wherein the process comprises:
(i) combining at least one (Compound II)

with at least one halogenating agent to produce at least one (Compound III)

(ii) combining the at least one Compound III with at least one cyanating agent to produce at least one (Compound IV)

(iii) combining the at least one Compound IV with at least one first precipitating agent; and
(iv) combining the at least one Compound IV with at least one hydrating agent and/or at least one hydrating catalyst to produce the at least one Compound I,
wherein $R^1$ and $R^5$ each independently represent a hydrogen, a $C_1$-$C_6$ alkyl, a hydroxy, or a $C_1$-$C_6$ alkoxy;
wherein $R^2$, $R^3$, and $R^4$ each independently represent a hydrogen, a $C_1$-$C_6$ alkyl, or a $C_1$-$C_6$ alkoxy;
wherein $R^6$ and $R^7$ each independently represent a hydrogen, a $C_1$-$C_6$ alkyl, a protecting group, or a directing group;
wherein X represents a halo moiety or a halo-like moiety;
wherein at least one of $R^1$ and $R^5$ represent a hydrogen; and
provided that in Compound II, $R^7$ represents a protecting group or a directing group, and either
(1) prior to step (ii), the at least one Compound III is combined with at least one deprotecting agent such that the protecting group or directing group represented by $R^7$ is replaced with a hydrogen or a $C_1$-$C_6$ alkyl, or
(2) prior to step (iii), the at least one Compound IV is combined with at least one deprotecting agent such that the protecting group or directing group represented by $R^7$ is replaced with a hydrogen or a $C_1$-$C_6$ alkyl.

Also provided are such processes wherein prior to step (iv), the at least one Compound IV is combined with at least one second precipitating agent to precipitate the at least one Compound IV.

Also provided are such processes wherein prior to step (ii), the at least one Compound III is combined with at least one deprotecting agent such that the protecting group or directing group represented by $R^7$ is replaced with a hydrogen or a $C_1$-$C_6$ alkyl and the at least one Compound III is combined with at least one third precipitating agent to precipitate the at least one Compound III.

Also provided are such processes wherein prior to step (iii), the at least one Compound IV is combined with at least one deprotecting agent such that the protecting group or directing group represented by $R^7$ is replaced with a hydrogen or a $C_1$-$C_6$ alkyl and the at least one Compound IV is combined with at least one third precipitating agent to precipitate the at least one Compound IV.

Also provided are such processes wherein at least one Compound II is produced by a process comprising combining at least one (Compound V)

with at least one protecting agent to produce at least one Compound II,
wherein in Compound V, $R^1$ and $R^5$ each independently represent a hydrogen, a $C_1$-$C_6$ alkyl, a hydroxy, or a $C_1$-$C_6$ alkoxy; $R^2$, $R^3$, and $R^4$ each independently represent a hydrogen, a $C_1$-$C_6$ alkyl, or a $C_1$-$C_6$ alkoxy; and $R^{6'}$ and $R^{7'}$ each independently represent a hydrogen or a $C_1$-$C_6$ alkyl.

In one embodiment of this invention X represents a halo moiety or a halo-like moiety.

In another embodiment, at least one of $R^1$, $R^2$, $R^3$, $R^4$, or $R^5$ represents a $C_1$-$C_6$ alkoxy.

In yet another embodiment, at least two of $R^1$, $R^2$, $R^3$, $R^4$, and $R^5$ each independently represent a $C_1$-$C_6$ alkoxy.

In yet another embodiment, at least three of $R^1$, $R^2$, $R^3$, $R^4$, and $R^5$ each independently represent a $C_1$-$C_6$ alkoxy.

In another embodiment, $R^2$ and $R^4$ each independently represent a $C_1$-$C_6$ alkoxy, and $R^1$ and $R^3$ each represent a hydrogen.

In one embodiment, the $C_1$-$C_6$ alkoxy is a methoxy.

In one embodiment, in Compound II, $R^2$ and $R^4$ each independently represent a $C_1$-$C_6$ alkoxy, $R^1$ and $R^3$ each represent a hydrogen, and $R^7$ represents trifluoroacetyl.

In one embodiment, a process according to this invention comprises:

(i) protecting 3,5-dimethoxyaniline with a protecting agent to produce a protected 3,5-dimethoxyaniline;

(ii) halogenating the protected 3,5-dimethoxyaniline with a halogenating agent to produce a halogenated protected 3,5-dimethoxyaniline;

(iii) cyanating the halogenated protected 3,5-dimethoxyaniline with a cyanating agent to produce a cyanated protected 3,5-dimethoxyaniline;

(iv) deprotecting the cyanated protected 3,5-dimethoxyaniline; and (v) hydrating the deprotected cyanated 3,5-dimethoxyaniline to produce 2-amino-4,6-dimethoxybenzamide.

In one embodiment, a process according to this invention comprises:

(i) protecting 3,5-dimethoxyaniline with a protecting agent to produce a protected 3,5-dimethoxyaniline;

(ii) halogenating the protected 3,5-dimethoxyaniline with a halogenating agent to produce a halogenated protected 3,5-dimethoxyaniline;

(iii) cyanating the halogenated protected 3,5-dimethoxyaniline with a cyanating agent to produce a cyanated protected 3,5-dimethoxyaniline;

(iv) deprotecting the cyanated protected 3,5-dimethoxyaniline and inducing precipitation to produce a precipitate comprising the cyanated 3,5-dimethoxyaniline; and (v) hydrating the precipitate comprising the cyanated 3,5-dimethoxyaniline to produce 2-amino-4,6-dimethoxybenzamide.

In one embodiment, a process according to this invention comprises:

(i) protecting a 3,5-dimethoxyaniline with a protecting agent to produce a protected 3,5-dimethoxyaniline;

(ii) halogenating the protected 3,5-dimethoxyaniline with a halogenating agent to produce a halogenated protected 3,5-dimethoxyaniline;

(iii) cyanating the halogenated protected 3,5-dimethoxyaniline with a cyanating agent to produce a cyanated protected 3,5-dimethoxyaniline;

(iv) deprotecting and precipitating the cyanated protected 3,5-dimethoxyaniline to produce a first precipitate comprising the cyanated 3,5-dimethoxyaniline;

(v) re-precipitating the first precipitate comprising the cyanated 3,5-dimethoxyaniline to produce a second precipitate comprising the cyanated 3,5-dimethoxyaniline; and (vi) hydrating the second precipitate comprising the cyanated 3,5-dimethoxyaniline to produce 2-amino-4,6-dimethoxybenzamide.

In another embodiment, a process according to this invention comprises:

(i) protecting a 3,5-dimethoxyaniline with a protecting agent to produce a protected 3,5-dimethoxyaniline;

(ii) halogenating the protected 3,5-dimethoxyaniline with a halogenating agent to produce a halogenated protected 3,5-dimethoxyaniline;

(iii) deprotecting the halogenated protected 3,5-dimethoxyaniline to produce a halogenated 3,5-dimethoxyaniline;

(iv) precipitating the halogenated 3,5-dimethoxyaniline;

(v) cyanating the halogenated 3,5-dimethoxyaniline with a cyanating agent to produce a cyanated 3,5-dimethoxyaniline;

(vi) precipitating the cyanated 3,5-dimethoxyaniline, and (vii) hydrating the precipitated cyanated 3,5-dimethoxyaniline to produce 2-amino-4,6-dimethoxybenzamide.

As used herein, "cyano" or "nitrile" refers to a —CN.

As used herein, halo moiety or halo-like moiety refers to chloro (Cl), bromo (Br), iodo (I), triflate (-OTf), tosylate (-OTs), or mesylate (-OMs).

As used herein, "alkyl" refers to a saturated straight, branched, or cyclic, primary, secondary, or tertiary hydrocarbon.

As used herein, "hydroxy" refers to a hydroxyl (—OH) moiety.

As used herein, "alkoxy" or "alkyloxy" refers to an alkyl moiety having an oxygen moiety attached thereto, e.g. methoxy, ethoxy, n-propoxy, sec-butoxy, t-butoxy, pentoxy, n-hexyloxy and the like.

As used herein, "carboxamide" or "amide" refers to —CONH$_2$.

As used herein, "intermediate" refers to any of Compounds II, III, or IV.

In another aspect, the invention provides processes for precipitating and/or re-precipitating at least one intermediate produced in the synthesis of Compound I.

The invention also provides a process for the synthesis of Compound I comprising conducting two or more of the process steps in a one-pot process.

In one embodiment, the steps of protecting, halogenating, cyanating, and deprotecting, as described herein, are carried out in a one-pot process.

It is to be understood that one skilled in the art of organic synthesis could follow the processes described or exemplified herein to prepare analogues or derivatives of 2-amino-4,6-dimethoxybenzamide. It is the object of the present invention to provide a novel and improved process for the synthesis of 2-amino-4,6-dimethoxybenzamide, which is useful as an intermediate to several therapeutic pharmaceutical compounds, such as cardiovascular agents.

These and other features of this invention will be further apparent from the ensuing description, drawings, and appended claims.

BRIEF DESCRIPTION OF THE DRAWINGS

In each of the above figures, like numerals are used to refer to like or functionally like parts among the several figures.

Protecting Step

The process step wherein at least one Compound II is produced by a process comprising combining at least one Compound V with at least one protecting agent to produce at least one Compound II, can be referred to as a "protecting step."

"Protecting agent" refers to any compound or groups of compounds that protects functional groups from unwanted reactions. For example, the protecting agent can protect $R^5$ of compound V during production of Compound II, or can protect $R^5$ of compound II during the halogenating step.

"Protective group" or "protecting group" refers to a protecting agent or part of a protecting agent that is attached to Compounds II, III, IV, or I. A protecting group selectively blocks a reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen present in the reactants. Desirably the protecting group exhibits the following characteristics: (i) reacts selectively with the desired functionality in good yield to give a protected substrate that is stable to the projected reactions for which protection is desired; (ii) is selectively removable from the protected substrate to yield the desired functionality; and (iii) is removable in good yield by reagents compatible with the other functional group(s) present or generated in such projected reactions. "Directing group" refers to a protecting agent or part of a protecting agent that influences the reactivity of a compound such that a chemical reaction involving the compound can occur with altered regioselectivity of the compound. A wide variety of protecting groups/directing groups are known to those skilled in the art of organic synthesis. Non-limiting examples of suitable protecting groups/directing groups can be found in Wuts et al. (2007) Greene's Protective Groups in Organic Synthesis, 4th Ed. (John Wiley & Sons, Inc., New York). For example, the terms "amino-protecting group" and "nitrogen protecting group" are used interchangeably herein and refer to those organic groups intended to protect the nitrogen atom against undesirable reactions during synthetic procedures. When referring to a protecting agent, one skilled in the art would understand which portion of the protecting agent will be attached, i.e. the protecting group, to the compound to be protected. Alternatively, when referring to a protecting group, one skilled in the art could deduce the necessary protecting agent to achieve the resulting protecting group. For example, trifluoroacetic anhydride may be referred to as the protecting agent and trifluoroacetyl is the protecting group. In another example, an acid chloride may be referred to as the protecting agent; for example benzoyl chloride can be referred to as the protecting agent, in which case benzoyl is the protecting group. Thus, for the purposes of this invention, "protecting group", "directing group", "protective group", or "protecting agent" may be used interchangeably and one skilled in the art would understand the relationship of the protecting agent to the protecting group or directing group. When referring to a protecting agent it includes all of the resulting protecting group or directing group and when referring to a protecting group or directing group, it also includes all of the protecting agent to create the resulting protecting group. Non-limiting exemplary protecting agent or its corresponding protecting groups or directing groups include acetyl, monohaloacetyl, dihaloacetyl, and trihaloacetyl (wherein the halo moiety may be the same or different for each dihaloacetyl and trihaloacetyl group), acetamido, benzyl (Bn), benzoyl (Bz), benzyloxycarbonyl (carbobenzyloxy, CBZ), p-methoxybenzyloxycarbonyl, p-nitrobenzyloxycarbonyl, tert-butoxycarbonyl (BOC), t-butyldimethylsilyl (TBDMS), 9-fluorenylmethyloxycarbonyl (Fmoc), other protecting group of the like, and combinations thereof. The term "protected" refers to a compound where at least one of its functional group is a protecting group or a directing group.

In one embodiment, the protecting group or directing group is an acetyl.

In another embodiment, the protecting group or directing group is a monohaloacetyl.

In another embodiment, the protecting group or directing group is a dihaloacetyl.

In another embodiment, the protecting group or directing group is a trihaloacetyl.

In another embodiment, the protecting group or directing group is trifluoroacetyl. It has been discovered that the trifluoroacetyl protecting/directing group results in an improved selectivity over the acetyl protecting/directing group during the halogenating step.

In one embodiment, the preparation for the synthesis of Compound I comprises combining Compound V with at least one protecting agent to produce a protected Compound II. It is to be understood that one skilled in the art of organic synthesis could follow the methods described or exemplified herein to determine if providing an already protected Compound II, or protecting a Compound V to produce a protected Compound II, is necessary to synthesize Compound I. The protecting step reaction can be carried out under any reaction time, pressure, temperature, solvent, pH condition, concentration, reagents ratio/amount, and any other chemical reaction conditions that are suitable to provide the desired protecting/directing effect. It is understood that one skilled in the art, given the teachings of this specification, can determine and/or optimize the reaction time, pressure, temperature, solvent, pH condition, concentration, reagent ratio/amount, and any other chemical reaction conditions suitable for the protecting step.

Figure 1:
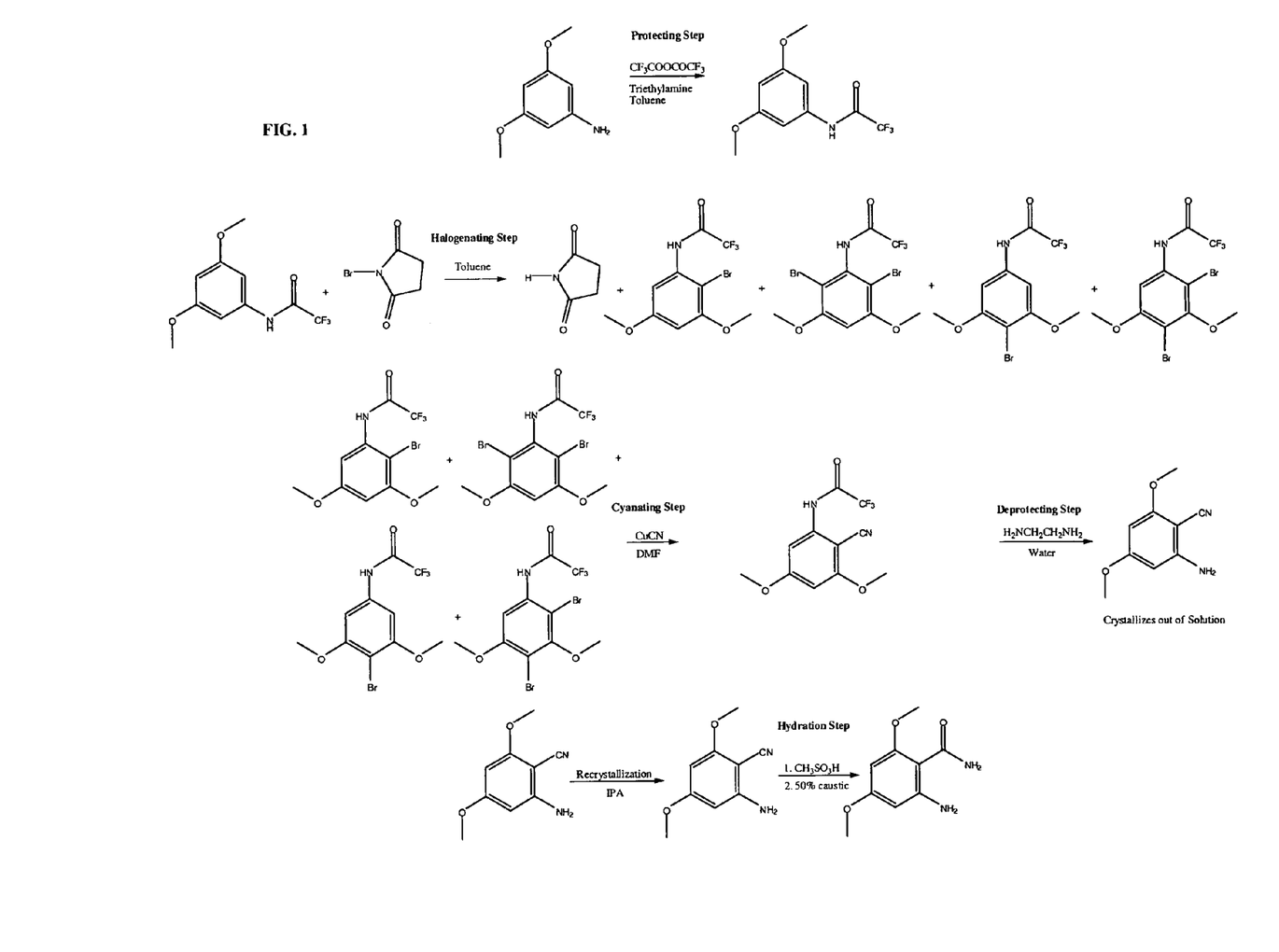
FIG. 1 is an illustration of a process according to this invention for the preparation of 2-amino-4,6-dimethoxybenzamide.
Figure 2:
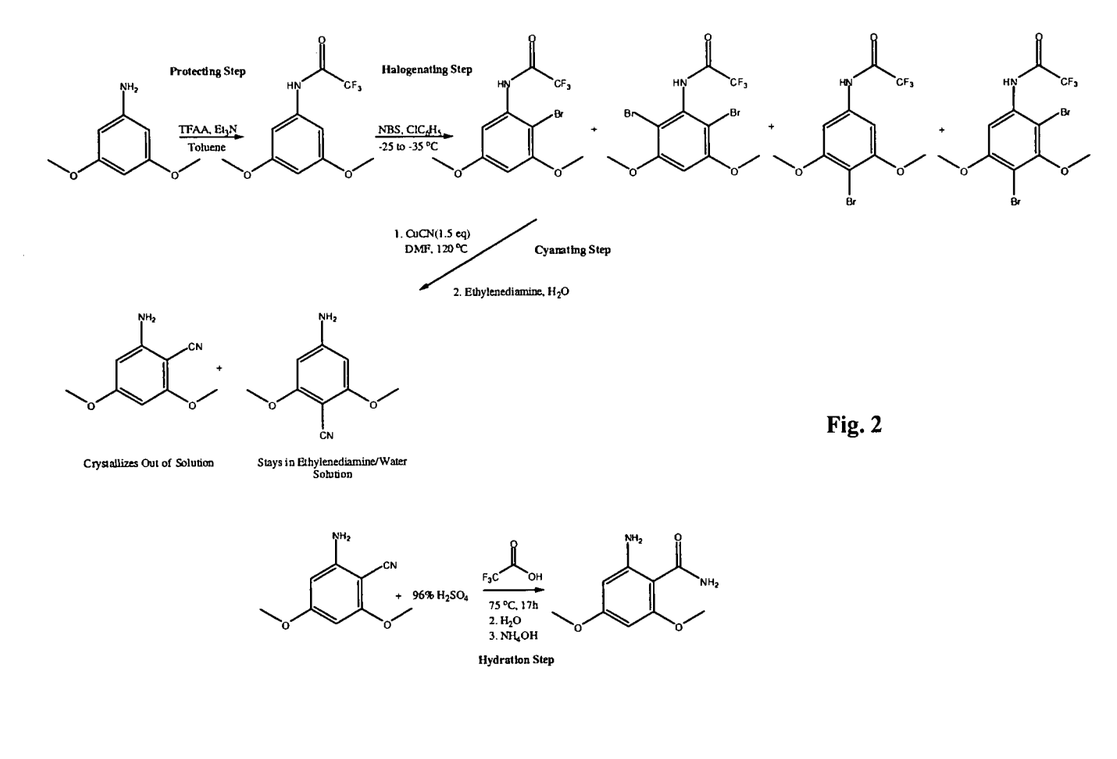
FIG. 2 is another illustration of a process according to this invention for the preparation of 2-amino-4,6-dimethoxybenzamide.

In one example, Compound I is 2-amino-4,6-dimethoxybenzamide and Compound V is 3,5-dimethoxyaniline. As seen in FIG. 1, the synthesis of 2-amino-4,6-dimethoxybenzamide comprises protecting 3,5-dimethoxyaniline with at least one protecting agent to produce a protected Compound II.

The protecting step in this example comprises combining 3,5-dimethoxyaniline with trifluoroacetic anhydride using triethylamine in toluene to produce a protected Compound II, or in this example 3,5-dimethoxyaniline produces 3,5-dimethoxytrifluoroacetanilide. Methyl tertiary-butyl ether (MtBE) can be used as a solvent in place of, or in addition to, toluene. Other suitable solvents may also be used. Given the teachings of this disclosure, one skilled in the art can select one or more other suitable solvents.

In one embodiment, a solution comprising the toluene or other solvent is taken directly to the next step, i.e. the halogenating step, following aqueous washes.

In another embodiment, a solution comprising the toluene or other solvent is taken directly to the next step, i.e. the halogenating step, without any aqueous washes.

Alternatively, one skilled in the art may remove, reduce, or increase the toluene or other solvent and/or other intermediates, and/or remove water before halogenating Compound II, e.g. removal of water via azeotropic distillation of the toluene or other solvent and water.

Depending on the starting Compound II and the desired benzamide Compound I to be synthesized, certain functional groups may need to be protected. One skilled in the art may use any known methods to protect certain functional group(s) of Compound II from unwanted reactions during the steps of halogenating, cyanating, and/or hydrating.

Providing a protected Compound II may not be required.

Halogenating Step

The process step wherein at least one Compound III is produced by a process comprising combining at least one Compound II with at least one halogenating agent to produce at least one Compound III, can be referred to as the halogenating step.

"Halogenating agent" refers to any compound that is capable of reacting with Compound II to add at least one halo moiety, a halo-like moiety, or substitute at least one of $R^1$, $R^2$, $R^3$, $R^4$, or $R^5$ of Compound II with at least one halo moiety or halo-like moiety.

"Halo-like" moiety refers to any group that behaves similarly to a halo moiety in terms of reactivity. Examples of halo-like moieties include triflate (-OTf), mesylate (-OMs), and tosylate (-OTs).

Examples of suitable halogenating agents include $I_2$, ICl, $ICl_3$, IBr, $Br_2$, BrCl, $Cl_2$, N-chlorosuccinimide, N-bromosuccinimide (NBS), 1,3-dibromo-5,5-dimethylhydantoin (DBDMH), TsCl, tosyl anhydride, MsCl, triflic chloride, and triflic anhydride. One skilled in the art of organic synthesis may utilize an alternate halogenating agent. Desirably, the amount of halogenating agent used should be stoichiometric with the desired product, as will be familiar to those skilled in the art.

In one embodiment, the halogenating agent is NBS.

In one embodiment, the halogenating agent is N-chlorosuccimimide.

In another embodiment, the halogenating agent is DBDMH.

In another embodiment, the halogenating agent is selected from $I_2$, ICl, $ICl_3$, IBr, $Br_2$, BrCl, and $Cl_2$.

In another embodiment, the halogenating agent is selected from TsCl, tosyl anhydride, MsCl, triflic chloride, and triflic anhydride.

It is understood that, given the teachings of this specification, one skilled in the art can determine and/or optimize the reaction time, pressure, temperature, solvent, pH condition, concentration, reagent ratio/amount, and any other chemical reaction conditions suitable for the halogenating step to add at least one halo moiety or halo-like moiety to Compound II.

In one embodiment, the halogenating step may be carried out at any temperature range above the freezing point and below the boiling point of the selected solvent. It is desirable to optimize the temperature and solvent conditions in accordance with solubility considerations of the Compound II when subjected to the halogenating agent.

In one embodiment, the temperature range is from about −65° C. to about 100° C.

In one another embodiment, the temperature range is from about −65° C. to about 50° C.

In another embodiment, the temperature range is from about −65° C. to about 10° C.

In another embodiment, the temperature range is from about −10° C. to about 10° C.

In yet another embodiment, the temperature range is from about −10° C. to about 5° C.

In yet another embodiment, the temperature range is from about −5° C. to about 5° C.

In yet another embodiment, the temperature range is from about 0° C. to about 5° C.

In one embodiment, as shown in FIG. 1, the protected aniline (3,5-dimethoxytrifluoroacetanilide) compound is reacted with at least one halogenating agent as shown, N-bromosuccinimide (NBS), at a temperature range from about −5° C. to 0° C. to produce halo isomers (e.g. bromo-3,5-dimethoxytrifluoroacetanilide isomers).

As illustrated, the halogenating step solvent can comprise toluene. MtBE and/or dimethylacetamide (DMAc) can be used as a halogenating step solvent in place of, or in addition to, toluene. Other suitable halogenating step solvents can also be used. Given the teachings of this disclosure, one skilled in the art can select one or more other suitable solvents.

The halogenating step produces various halo isomers. For example, as is illustrated by FIG. 1, the halogenating step can produce isomers wherein the halo, or as shown, the bromo, is at the 4-position, 2-position, both at the 2- and 4-positions, and both the 2- and 6-positions. It is understood that there could be other isomers produced depending on Compound II, the halogenating agents and conditions used.

It is an advantage of methods of this invention that in spite of the presence of any or all of the isomers created from the halogenating step, the desired 2-cyano isomer (Compound IV) is produced during the cyanating step.

In one embodiment, following the completion of the halogenating reaction, the succinimide by-products are removed by any known means in the arts, such as washing the batch with water.

In another embodiment, the solvent, e.g., toluene, may be removed using any known methods such as distillation or vacuum.

In another embodiment, a solvent exchange is completed to N',N'-dimethylformamide (DMF).

In another embodiment, the solution of brominated, protected aniline (bromo-3,5-dimethoxytrifluoroacetanilide) in DMF is used in the cyanating step.

In another embodiment, the halogenating step comprises reacting 3,5-dimethoxytrifluoroacetanilide with at least one halogenating agent such as N-bromosuccinimide (NBS) in chlorobenzene to produce 2-bromo-3,5-dimethoxytrifluoroacetanilide and its isomers.

In one embodiment, the isomers may be removed or separated from solution before the cyanating step.

In another embodiment, the isomers are not removed or separated from solution before conducting subsequent reaction process.

It has been found that the protecting step and the selection of the protecting agent can improve the regioselectivity of Compound III. In one embodiment, the protecting agent improves, or results in higher, regioselectivity of a 2-halo isomer of Compound III over the other isomers such as the 4-halo isomer.

In one embodiment, the halo moiety is bromo.

Cyanating Step

The process step wherein Compound IV is produced by the process comprising combining at least one Compound III with at least one cyanating agent to produce at least one Compound IV is referred to herein as the cyanating step.

In one embodiment, the cyanating step comprises combining the halo-isomers of the halogenating step with at least one cyanating agent to produce cyano-isomers.

In one embodiment, as exemplified in FIG. 1, the bromo-isomers of Compound III, including 2-bromo-3,5-dimethoxytrifluoroacetanilide, in DMF are combined with copper (I) cyanide at a temperature range from about 98° C. to about 120° C. to produce 2-amino-4,6-dimethoxybenzonitrile. Other isomers may also be produced. In another embodiment, $K_4Fe(CN)_6$, together with a suitable catalyst, such as CuI at greater than 100 mole %, is used as the cyanating agent.

In one embodiment, DMF is removed using any known means such as distillation to concentrate the batch.

In another embodiment, the concentrated DMF solution is transferred into a solution of ethylenediamine and water to perform the deprotecting step and removal of copper salts.

It has been discovered that isolation of Compound IV at temperatures near the higher end of the range disclosed herein results in yields near the lower end of the range disclosed herein.

In another embodiment, Compound IV, such as 2-amino-4,6-dimethoxybenzonitrile, is isolated by filtration and dried under a stream of nitrogen.

Using the teachings herein regarding the processes of this invention, the 2-isomer is isolated out of solution or precipitates out, while the non-favored isomers are not isolated out of the solution. It is an advantage of this invention that the desired isomer is isolated and the undesired isomers (4-, 2-/4-, and 2-/6-isomers), which are considered impurities, are not isolated.

In one embodiment, the cyanating step comprises precipitating 2-amino-4,6-dimethoxybenzonitrile. The process provided results in the precipitation of the desired 2-amino-4,6-dimethoxybenzonitrile intermediate product, resulting in lower isomeric impurities. As such, the one-pot process improves cost and time factors for improved efficiency without the need to purify and isolate at each intermediate reaction.

In one embodiment, Compound IV is combined with at least one deprotecting agent and first precipitating agent, such as ethylenediamine and water. In this embodiment, after the step of deprotecting or removal of the trifluoroacetyl group, the favored isomer, i.e. 2-amino-4,6-dimethoxybenzonitrile, precipitates out of solution while the other isomers remain in solution.

The cyanating step can be carried out under any reaction time, pressure, temperature, solvent, pH condition, concentration, reagents ratio/amount, and any other chemical reaction conditions that are suitable to add at least one cyano (—CN) moiety to Compound III or replace at least one halo moiety with at least one cyano group on Compound III. It is understood that one skilled in the art can determine and/or optimize the reaction time, pressure, temperature, solvent, pH condition, concentration, reagent ratio/amount, and any other chemical reaction conditions suitable for the cyanating step.

In one embodiment, the temperature range for the cyanating step may be from about 50° C. to about 155° C.

In another embodiment, the temperature range for the cyanating step may be from about 50° C. to about 120° C.

In yet another embodiment, the temperature range for the cyanating step may be from about 50° C. to about 105° C.

In yet another embodiment, the temperature range for the cyanating step may be from about 98° C. to about 105° C.

"Cyanating agent" refers to any compound which when reacted with Compound III can replace at least one halo moiety with a cyano group or add at least one cyano moiety to Compound III. Non-limiting examples of cyanating agent includes $Zn(CN)_2$, CuCN, NaCN, KCN, $Cu(CN)_2$, $Ni(CN)_2$, iron cyanide and other agents of the like. Cyanating may be carried out with or without a catalyst, e.g., a cyanating agent may comprise a catalyst.

In one embodiment, the cyanating agent is CuCN.

In another embodiment the cyanating agent comprises $K_4Fe(CN)_6$ and CuI.

In another embodiment the cyanating agent comprises $Na_4Fe(CN)_6$ and CuBr.

In another embodiment the cyanating agent comprises $K_4Fe(CN)_6$ and CuBr.

In another embodiment the cyanating agent comprises $Na_4Fe(CN)_6$ and CuI.

Deprotecting Step

The process step wherein the protecting group or directing group represented by $R^7$ is replaced such that $R^7$ represents a hydrogen or a $C_1$-$C_6$ alkyl, is referred to herein as the deprotecting step.

"Deprotecting" refers to the removal of at least one protecting group or directing group. "Deprotecting agent" refers to any compound that can remove at least one protecting group or directing group. Various methods and conditions to deprotect a compound are generally known to those skilled in the art. Non-limiting deprotecting agents include ethylenediamine, ammonia, ethanolamine, and methylamine.

In one embodiment, the deprotecting step is carried out before the cyanating step.

In one embodiment, the deprotecting step is carried out after the cyanating step.

In one embodiment, the deprotecting step is carried out simultaneously with the cyanating step.

The deprotecting step can also be carried out partially before the cyanating step and/or partially during the cyanating step and/or partially after the cyanating step.

It is an advantage of this invention that any of the cyanating step and deprotecting step and precipitating step can be conducted in a one-pot process.

Precipitating Step

The process step wherein the at least one Compound III is combined with at least one third precipitating agent, or wherein the at least one Compound IV is combined with at least one first or third precipitating agent, is referred to herein as the precipitating step.

As used herein, "first precipitating agent" refers to any substance that promotes or causes a Compound IV to precipitate out of solution. The resulting precipitate can comprise crystalline structures and/or amorphous structures. A non-limiting example of a suitable first precipitating agent is water. In light of the teachings of this specification, other suitable first precipitating agents will be familiar to those skilled in the art.

As used herein, "third precipitating agent" refers to any suitable non-polar solvent or other suitable substance that promotes or causes a Compound III or a Compound IV to precipitate out of solution. The resulting precipitate can comprise crystalline structures and/or amorphous structures. A non-limiting example of a suitable third precipitating agent is heptane. In light of the teachings of this specification, other suitable third precipitating agents will be familiar to those skilled in the art.

In one embodiment, deprotecting and precipitating are done in the same step.

In one embodiment, ethylenediamine and heptane are used to promote deprotecting and precipitating of Compound III.

In one embodiment, ammonia and heptane are used to promote deprotecting and precipitating of Compound III.

In one embodiment, ethanolamine and heptane are used to promote deprotecting and precipitating of Compound III.

In one embodiment, methylamine and heptane are used to promote deprotecting and precipitating of Compound III.

In one embodiment, ethylenediamine and water are used to promote deprotecting and precipitating of Compound IV.

In one embodiment, ammonia and water are used to promote deprotecting and precipitating of Compound IV.

In one embodiment, ethanolamine and water are used to promote deprotecting and precipitating of Compound IV.

In one embodiment, methylamine and water are used to promote deprotecting and precipitating of Compound IV.

In one embodiment, the precipitating step is carried out after the cyanating and deprotecting steps.

Alternatively, one skilled in the art may precipitate and/or isolate the intermediate products of Compounds III or IV at any desired time during processes of this invention.

Re-Precipitating Step

The optional process step wherein at least one Compound IV is combined with at least one second precipitating agent is referred to herein as the "re-precipitating step".

As used herein, "second precipitating agent" refers to any substance that promotes or causes a Compound IV to precipitate out of solution, following at least one previous precipitation of Compound IV with either a first precipitating agent or a third precipitating agent, in accordance with this invention. The resulting precipitate can comprise crystalline structures and/or amorphous structures. A non-limiting example of a suitable second precipitating agent is isopropyl alcohol. In light of the teachings of this specification, other suitable second precipitating agents will be familiar to those skilled in the art.

In processes of this invention, the re-precipitating step may also result in purification of the Compound IV precipitate.

Hydrating Step

The process step wherein Compound I is produced by the process comprising combining at least one Compound IV with at least one hydrating agent and/or at least one hydrating catalyst to produce at least one Compound I is referred to herein as the hydrating step.

In one embodiment, the hydrating step comprises combining Compound IV with at least one hydrating agent and/or at least one hydrating catalyst to produce at least one Compound I is referred to herein as the hydrating step.

The hydrating step reaction can be carried out under any reaction time, pressure, temperature, solvent, pH condition, concentration, reagents ratio/amount, and any other chemical reaction conditions that are suitable to remove or substitute at least one cyano moiety from Compound IV. It is understood that one skilled in the art can determine and/or optimize the reaction time, pressure, temperature, solvent, pH condition, concentration, reagent ratio/amount, and any other chemical reaction conditions suitable for the hydrating step.

In one embodiment, the hydrating step comprises converting at least one cyano moiety into at least one carboxamide.

In one embodiment, the hydrating step may be carried out at a temperature range from about 70° C. to about 150° C.

In another embodiment, the hydrating step may be carried out at a temperature range from about 100° C. to about 115° C.

It is understood that the temperature used will affect the rate of reaction. A longer hydrating reaction time with low temperature may result in increased impurities, but desired product can still be achieved from the process provided. In addition, a higher temperature generally results in a faster rate of reaction, but will also have higher impurity profile. Thus, optimizing the time and temperature will result in an improved purity profile.

In one embodiment, the process for the synthesis of 2-amino-4,6-dimethoxybenzamide comprises hydrating 2-amino-4,6-dimethoxybenzonitrile with at least one hydrating agent such as methanesulfonic acid.

In one embodiment, the hydrating step further comprises re-precipitating 2-amino-4,6-dimethoxybenzonitrile before contacting it with a hydrating agent. The reaction is conducted for about two hours of heating (approximately 1-2 hours at temperatures between 100-115° C.).

In another embodiment, hydrating the nitrile compound further comprises adding water and dichloromethane (DCM) to the acidic mixture. The choice of solvent is not limited to the preceding examples, but is dependent on the structure of the compound of interest among other factors. One skilled in the art may use alternate solvents that do not react with the compound of interest, such as but not limited to ethyl acetate, isopropyl acetate, ether such as 2-methyltetrahydrofuran, alcohol such as isopropyl alcohol, and other solvents or combinations of solvents of the like.

In another embodiment, the hydrating step further comprises neutralizing the batch by contacting about 50% caustic and adjusting the pH range from about 3 to about 12. One skilled in the art may use an alternate neutralizing agent to adjust the pH as desired.

In one embodiment, the pH range may be from about 6.0 to about 8.0. In another embodiment, the pH range may be from about 6.5 to about 7.3.

In a further embodiment, the hydrating step further comprises an extracting step. The extracting step comprises extracting the aqueous layer with DCM three times and the organic layer is washed twice with water to remove methanesulfonate salts. Distillation of dichloromethane occurs to reduce the overall batch volume and the batch is slowly cooled to a temperature range from about 23° C. to about 28° C. MtBE is charged to the batch and it is further cooled down to a temperature range from about −5° C. to about 0° C. The product 2-amino-4,6-dimethoxybenzamide is isolated by any means such as by filtration and dried under a stream of nitrogen. One skilled in the art may use another type of solvent for extraction that does not adversely affect the reactions such as isopropyl acetate, ethyl acetate, isopropyl alcohol, 2-methyltetrahydrofuran, or combinations thereof. If a batch that is free of halogenated solvent is desired, a solvent exchange occurs until there is less than 1% halogenated solvent remaining in the pot. Alternatively, a non-halogenated solvent may be used following neutralization, thereby potentially eliminating the need for solvent exchange. The volume is reduced via distillation until the desired volume range of IPAc, IPA, ethyl acetate, methyl THF, or alternate solvent is achieved. The use of an appropriate anti-solvent, such as MtBE or heptane, is optional. However, yield improvement is observed with an appropriate anti-solvent.

In another embodiment, 2-amino-4,6-dimethoxybenzamide is prepared comprising hydrating 2-cyano-3,5-dimethoxytrifluoroacetanilide with a hydrating agent such as trifluoroacetic acid as shown below.

In one embodiment, the preparation of 2-amino-4,6-dimethoxybenzamide comprises deprotecting 2-cyano-3,5-dimethoxytrifluoroacetanilide to produce a 2-amino-4,6-dimethoxybenzonitrile.

"Hydrating agent" refers to any compound which when combined with Compound N can convert at least one cyano group into a carboxamide group or hydrate the triple bond of the cyano group. Hydrating agent also includes hydrating catalysts. The term "hydrating catalyst" refers to any compound that promotes and/or assists in hydrating Compound IV to Compound I. Non-limiting examples of hydrating agents include water, ferric nitrate, alcohols, acids such as sulfuric acid, trifluoroacetic acid, methanesulfonic acid, phosphoric acid such as polyphosphoric acid, bases such as NaOH, KOH, cesium hydroxide, barium hydroxide, metal catalyst, the like, and combinations thereof.

In one embodiment, the hydrating step converts the cyano group into a carboxamide group while minimizing the amount of carboxylic acid produced.

In another embodiment, the hydrating step is carried out under acidic reaction conditions.

In another embodiment, the hydrating step may also be carried out under basic reaction conditions.

The reactions of the synthetic methods claimed herein are carried out in suitable solvents which can be readily selected by one of skill in the art of organic synthesis, said suitable solvents generally being any solvent which is substantially non-reactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or in a combination of two of more solvents. Depending on the particular reaction step, suitable solvents for a particular reaction step can be selected by one skilled in the art.

The process represented in FIG. 1 is meant to be illustrative of the present invention and is not meant to be construed as limiting the invention's scope. One skilled in the art understands that the process provided herein may produce various minor products that can also be generated by the reactions of the present invention. Thus, the process of the invention allows for streamlined processing since the intermediates after each step can be used directly in the subsequent reactions without having to be isolated or purified. Alternatively, one skilled in the art may purify and isolate the intermediates before the subsequent reactions.

The functional groups or moieties of the present invention include substituted or non-substituted, protected or non-protected moiety. When a particular group is "substituted" that group may have one or more substituents, from one to five substituents, from one to three substituents, from one to two substituents, independently selected from the list of substituents.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

Under standard nomenclature, the terminal portion of the designated side chain is described first, followed by the adjacent functionality toward the point of attachment. The nomenclature used herein for the functional groups or moieties are not limited to the standard placement of the groups but can be in any order so long as it does not violate any chemical properties.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

Any of the functional groups provided herein maybe be further substituted with any other known functional groups known in the art that does not adversely affect the stability of the compounds or the reactions provided herein.

It is also understood that the listed solvents and reagents may be used singularly or in combination with other solvents and reagents so long as the combinations do not adversely affect the stability of the compounds or the reactions provided herein.

The following examples are presented for purposes of illustration, and are not intended to impose limitations on the scope of this invention.

EXAMPLE 1

3,5-dimethoxytrifluoroacetanilide

To a 2-liter jacketed flask was loaded 3,5-dimethoxyaniline (120 g), toluene (1335 g) and triethylamine (87 g). The mixture was stirred at 18-20° C. until all solids dissolved. Trifluoroacetic anhydride (185 g) was added over at least 1 hour maintaining a reaction temperature of 18-25° C. The reaction was stirred for at least 1 hour and then checked by HPLC for reaction completion. Water (250 g) was loaded to the batch and the reaction was heated to 40-45° C. and stirred for at least 10 minutes. The agitation was stopped and the phases were separated. The bottom aqueous phase was removed and water (250 g) was loaded to the toluene product layer. The batch was stirred at 40-45° C. for at least 10 minutes and the phases were separated by removing the bottom aqueous phase. The 3,5-dimethoxytrifluoroacetanilide product toluene solution was then cooled to less than 0° C. in preparation for the bromo-3,5-dimethoxytrifluoroacetanilide step of the process.

EXAMPLE 2 bromo-3,5-dimethoxytrifluoroacetanilide

The 3,5-dimethoxytrifluoroacetanilide toluene solution contained in a 2-liter jacketed flask was cooled to −5 to 0° C. N-bromosuccinimide solid (145 g) was loaded to the cold 3,5-dimethoxytrifluoroacetanilide slurry in 5 to 10 gram portions over the course of at least 1 hour. A temperature of less than 0° C. was maintained during the addition. Upon completion of the addition the batch was allowed to warm to 15-23° C. and was stirred for at least 1 hour. The reaction completion was monitored by HPLC. When the reaction was complete, water (235 g) was loaded to the batch and the reaction heated to 35-45° C. and held for at least 10 minutes. The agitation was stopped and the phases were allowed to separate. The bottom aqueous phase was removed and water (235 g) was loaded to the bromo-3,5-dimethoxytrifluoroacetanilide toluene solution. The batch was agitated at 35-45° C. for at least 10 minutes and the phases were separated by removal of the lower aqueous phase. The bromo-3,5-dimethoxytrifluoroacetanilide toluene solution was transferred to a 2-liter four-neck round bottom flask fitted with a distillation apparatus and a heating mantle. The solution was heated to reflux and toluene was distilled until a pot temperature of 125-140° C. was obtained. The batch was cooled to less than 80° C. under nitrogen and N',N'-dimethylformamide (DMF) (1215 g) was loaded to the pot. The batch was agitated and cooled to less than 80° C. This solution was used in the 2-amino-4,6-dimethoxybenzonitrile step of the process.

EXAMPLE 3

Cyanating bromo-3,5-dimethoxytrifluoroacetanilide

To the bromo-3,5-dimethoxytrifluoroacetanilide/DMF solution in a 2-liter round bottom flask was loaded 89 grams of copper cyanide (CuCN). The batch was heated to 98-120° C. and held for at least 6 hours. The reaction completion was checked by HPLC analysis. Upon completion the reaction was cooled to less than 60° C. and vacuum was applied to the vessel and DMF was distilled. The distillation was continued to a pot volume of approximately 570 mL. The pot residue was cooled to less than 40° C.

Deprotecting 2-cyano-3,5-dimethoxytrifluoroacetanilide

To a separate 2-liter jacketed flask was loaded water (1065 g) and ethylenediamine (390 g). The aqueous solution was heated to 50-55° C. and held. The 2-cyano-3,5-dimethoxytrifluoroacetanilide/DMF pot residue from the previous step was loaded to the aqueous mixture over at least 15 minutes. The reaction solution was stirred at 50-55° C. for at least 2 hours. The reaction completion check analysis was performed by HPLC. Upon reaction completion the batch was adjusted to 35-37° C. and held for slurry formation. The resulting slurry was cooled slowly to 5-15° C. over at least 2 hours. The batch was held at 5-15° C. for 2 hours and then the 2-amino-4,6-dimethoxybenzonitrile product was isolated by filtration. The 2-amino-4,6-dimethoxybenzonitrile cake was washed with water to remove the mother liquor. The final wet cake was dried and analyzed by HPLC. The process produced 123 grams of 2-amino-4,6-dimethoxybenzonitrile product in a yield of 88% from the starting 3,5-dimethoxyaniline.

EXAMPLE 4

Re-precipitation of 2-amino-4,6-dimethoxybenzonitrile

To a 1-liter four neck round bottom flask was loaded 2-amino-4,6-dimethoxybenzonitrile (90 g) and isopropyl alcohol (720 mL). The flask was fitted with a condenser and a heating mantle. Carbon (1.8 g) was added to the agitating mixture and the batch was heated to reflux (82-83° C.). The batch was held for 1 hour at reflux and then cooled to 75-77° C. and held for at least 6 hours. The carbon was then filtered away and the filtrate was collected in a clean 1-liter four neck round bottom flask. The filtrate was cooled slowly to 60-62° C. and held until re-precipitation occurred. The resulting slurry was cooled slowly to 0-5° C. over at least 2 hours. The batch was held at 0-5° C. for at least 0.5 hours and filtered to harvest the product. The 2-amino-4,6-dimethoxybenzonitrile cake was washed with isopropyl alcohol and dried in a vacuum oven at 50° C. and 22 inches of vacuum. The process produced 83.8 grams of purified 2-amino-4,6-dimethoxybenzonitrile in 84% yield.

EXAMPLE 5

2-amino-4,6-dimethoxybenzamide 2-amino-4,6-dimethoxybenzonitrile (10.0 g, 0.056 mol, 1 eq.) was charged to a 1-L glass vessel under $N_2$ atmosphere and agitation was started. Methanesulfonic acid (120 mL, 1.848 mol, 33 eq.) was charged to the vessel and the reaction was heated at 100-115° C. for 1-2 hours. Upon verification of reaction completion by HPLC, the batch was cooled to 20-30° C. Upon cooling, dichloromethane (67 mL) and cool water (164 mL) (5-10° C.) were added to keep the temperature in the range of 10-30° C. 50% caustic (94 mL) was charged to the vessel using an addition funnel while maintaining 0-30° C. Fine pH adjustment to 6.5 to 7.3 was completed using either 32% HCl or 50% caustic. Upon equilibration, the first organic phase cut was performed. The aqueous layer was extracted two additional times with DCM (74 mL and 57 mL respectively). Dichloromethane (54 mL) was added to the combined organic layers and the organic layer was washed with water (143 mL) to remove methanesulfonate salts. Dichloromethane (16 mL) was added to the combined organic layers and the organic layer was washed once more with water (143 mL) to remove methanesulfonate salts. The batch was distilled using (5-10 inches Hg) vacuum to a pot volume of 4.5 volumes DCM (45 mL). The contents of the vessel were stirred for 1 hour at 38° C. The vessel was cooled to 23-28° C. over 1 hour with slow agitation. When clouding was observed, the vessel was slowly charged with 14.4 volumes MtBE (144 mL) and the batch was agitated for 30 min at 25° C. (ratio of DCM/MtBE is 1:3.2; total volumes of solvent is 18.9). The batch was slowly cooled to between –5° C. and 5° C. over at least 3 hours. The batch was held for at least 1 hour between –5° C. and 0° C. Precipitation was verified through collection of at least two samples from the liquor to determine the amount of 2-amino-4,6-dimethoxybenzamide remaining in solution. The batch was isolated by filtration and the wet cake washed with a cold (0° C.) mixture of 1:4 DCM/MtBE (51 mL). The 2-amino-4,6-dimethoxybenzamide wet cake was dried in a vacuum oven (40-45° C., 25 inches Hg) to give 2-amino-4,6-dimethoxybenzamide (8.33 g, 0.0425 mol, 75.7% yield; 53% yield over 5 steps from 3,5-dimethoxyaniline). Use of an alternate solvent to dichloromethane has been studied and performs in a similar fashion to dichloromethane. Examples of alternate solvents include, but are not limited to esters like isopropyl acetate and ethyl acetate, and ethers like 2-methyltetrahydrofuran. In addition, alternate precipitation systems with or without anti-solvent have also been examined. The precipitation system may include, but is not limited to esters like isopropyl acetate, ethers like 2-methyltetrahydrofuran, and alcohols like isopropyl alcohol. The yield range from these modifications in the experimental procedure is 72-79%. In addition, purity of the desired compound is consistently over 99%.

EXAMPLE 6

2-amino-4,6-dimethoxybenzamide 2-amino-4,6-dimethoxybenzonitrile (50.0 g, 0.2805 mol, 1 eq.) was charged to a 3-L glass vessel under $N_2$ atmosphere and agitation was started. Methanesulfonic acid (537 mL, 8.29 mol, 29.5 eq.) was charged to the vessel and the reaction was heated at 100-115° C. for 1-2 hours. Upon verification of reaction completion by HPLC, the batch was cooled to 20-30° C. Upon cooling, dichloromethane (334 mL) and cool water (807 mL) (5-10° C.) was added to keep the temperature in the range of 10-30° C. 50% caustic (423 mL) was charged to the vessel using an addition funnel while maintaining 0-30° C. Fine pH adjustment to 6.5 to 7.5 was completed using either 32% HCl or 50% caustic, or diluted solutions thereof. Upon equilibration, the first organic phase cut was performed. The aqueous layer was extracted two additional times with DCM (371 mL and 286 mL respectively). Dichloromethane (271 mL) was added to the combined organic layers and the organic layer was washed with water (714 mL) to remove methanesulfonate salts. Dichloromethane (79 mL) was added to the combined organic layers and the organic layer was washed once more with water (714 mL) to remove methanesulfonate salts. The batch was distilled using (5-10 inches Hg) vacuum to a pot volume of 6 volumes DCM (300 mL). Solvent exchange with isopropyl acetate (2 exchanges of 402 mL and 484 mL respectively) was completed when less than 1-2% DCM remained and the pot volume was between 400-450 mL. The contents of the vessel were stirred for 1 hour at 85-90° C. The vessel was cooled to 50° C. over at least 2 hours with slow agitation. The vessel was slowly charged with MtBE (250 mL) and the batch was agitated for 30 min at 50° C. The batch was slowly cooled to 30° C. over at least 1 hour. The batch was cooled to –5° C. and 5° C. over at least 2 hours. The batch was held between –5° C. and 5° C. over at least 1 hour. Precipitation was verified through collection of at least two samples from the liquor to determine the amount of 2-amino-4,6-dimethoxybenzamide remaining in solution. The batch was isolated by filtration and the wet cake washed with cold (0° C.) MtBE (100 mL). The 2-amino-4,6-dimethoxybenzamide wet cake was dried in a vacuum oven (40-45 C, 25 inches Hg) to give 2-amino-4,6-dimethoxybenzamide (42.79 g, 0.218 mol, 77.7% yield; 54.5% yield over 5 steps from 3,5-dimethoxyaniline). Variations of the volumes of solvent used during extraction and the precipitation portions in this example may give improved or reduced yield and/or purity. One skilled in the art may modify these conditions for the desired result.

EXAMPLE 7

3,5-dimethoxytrifluoroacetanilide

To a 1-L jacketed flask, equipped with a mechanical stirrer and a thermocouple was charged finely ground 3,5-dimethoxyaniline (51.20 g, 0.33 mol), triethylamine (38.21 g, 0.38 mol) and toluene (246.70 g). The chiller was set to 15° C. and when the reaction temperature reached that value trifluoroacetic anhydride (73.51 g, 0.35 mol) was added over 1.5 hours maintaining the reaction temperature around 20° C. Water (124.69 g) was then added to the cooled (15° C.) solution and when the reaction mixture was cooled to 12° C. solids precipitated from the reaction. The biphasic solution was filtered and the solids agitated with water (326.38 g) for 15 minutes. The product was filtered, and dried to yield an off white solid (71.15 g, 85.4% yield).

EXAMPLE 8 bromo-3,5-dimethoxytrifluoroacetanilide

A solution of chlorobenzene (434.04 g) and 3,5-dimethoxytrifluoroacetanilide (50.03 g, 0.20 mol, 1.0 molar equivalents) was added to a 1-L flask equipped with a mechanical stirrer and thermocouple. The flask was cooled in an isopropyl alcohol bath and small amounts of dry ice were added to maintain the solution temperature in the flask at approximately −25° C. NBS (37.07 g, 0.20 mol, 1.04 molar equivalents) was added in small portions to the reaction mixture over 1.2 hours while maintaining the reaction temperature at −25 to −35° C. The solution was then warmed to 0-1° C. over 3.5 hours. A reaction sample was added to sodium thiosulfate solution and the organic layer analyzed by GC. Water (100.01 g) was added to the reaction mixture and the mixture was agitated. The aqueous layer was removed and the organic layer was then washed twice more with water (101.08, and 100.94 g). The solvent was removed by rotary evaporation in vacuo to yield an off-white solid (63.04 g).

EXAMPLE 9

2-cyano-3,5-dimethoxytrifluoroacetanilide

The crude brominated isomer mixture (40.06 g) was dissolved in DMF (234.79 g) in a 500 mL flask equipped with a thermocouple and mechanical stirrer. Cuprous cyanide (16.95 g) was added to the solution at room temperature. The dark solution was then heated to 120° C. and held at that reaction temperature for 4.25 hours. After the crude reaction mixture had cooled to room temperature the mixture was poured into an Erlenmeyer flask containing water (222.27 g) that was rapidly swirled as the solution was added. The solids that precipitated were filtered and washed with water (121.94 g). When the water wash from the solids was combined with the water/DMF solution additional solids were obtained. These solids were washed with water (122.16 g). A 1 L flask equipped with a mechanical stirrer and thermocouple was charged with water (292.32 g). Ethylenediamine (106.92 g)

was slowly added to the stirred solution. The combined reaction solids were fed into the stirred solution. After the addition had been completed, the reaction temperature was raised to 50° C. and that temperature maintained for 0.5 h. As the solution was cooled back to room temperature solids precipitated from the solution. These solids were filtered to yield the product (15.29 g).

EXAMPLE 10

2-amino-4,6-dimethoxybenzamide

Trifluoroacetic acid (6.52 g, 4.4 mL) was charged to a flask equipped with a magnetic stirring bar and thermocouple. Sulfuric acid (96%, 9.2 g, 5 mL) was charged to the flask. In small portions 2-amino-4,6-dimethoxybenzonitrile (1.01 g, ~76% pure) was charged to the mixed acid solution in the flask. A condenser was added and the solution was heated at 75° C. for 17 h. After the dark mixture had cooled to room temperature it was charged to water (9.79 g) cooled in a large ice bath while maintaining the reaction temperature below 10° C. Concentrated ammonium hydroxide (19.37 g) was added dropwise to the cooled solution (reaction temperature kept below 15° C.). The solution was then extracted two times with dichloromethane. The organic extracts were dried over $MgSO_4$ and evaporated to yield the desired product (0.45 g) as a light brown solid.

EXAMPLE 11

3,5-dimethoxytrifluoroacetanilide

To a 1-liter 3-neck round-bottom-flask with overhead stirring was loaded 3,5-dimethoxyaniline (50 g), triethylamine (50 mL), and MtBE (450 mL). The mixture was stirred and cooled with a methanol/ice bath at −20° C. Trifluoroacetic anhydride (50 mL) was added while maintaining a reaction temperature of less than 30° C. The reaction was checked by HPLC for reaction completion. The 3,5-dimethoxytrifluoroacetanilide product MtBE solution was then cooled to less than 0° C. in preparation for the bromo-3,5-dimethoxytrifluoroacetanilide step of the process.

EXAMPLE 12 bromo-3,5-dimethoxytrifluoroacetanilide

The 3,5-dimethoxytrifluoroacetanilide MtBE solution contained in a 1-liter 3-neck round-bottom-flask was cooled to −5 to 0° C. To a 125-mL Erlenmeyer flask was loaded DBDMH (47.5 g) and N,N-dimethylacetamide (55 mL). The DBDMH mixture was stirred to dissolution and charged to the cold 3,5-dimethoxytrifluoroacetanilide solution. A temperature of less than 0° C. was maintained during the addition. The batch was checked by HPLC for reaction completion. When the reaction was complete, the mixture was warmed to 40° C. and water (100 g) was loaded to the batch. The agitation was stopped and the phases were allowed to separate. The bottom aqueous phase was removed and water (25 g) was loaded to the bromo-3,5-dimethoxytrifluoroacetanilide MtBE solution. The batch was agitated at 40° C. and the phases were separated by removal of the lower aqueous phase. The flask was fitted with a Dean-Stark trap. The bromo-3,5-dimethoxytrifluoroacetanilide MtBE solution was heated to reflux and residual water was collected in the trap. When water stopped collecting in the trap, MtBE was distilled until a pot temperature of 75° C. was obtained. Heptane (500 mL) was loaded to the mixture. The batch was agitated and heated to 80° C. External heating was removed and the batch cooled to 20-25° C. The precipitated bromo-3,5-dimethoxytrifluoroacetanilide was isolated by filtration, washed with heptane (100 mL) and dried in a vacuum oven at 50° C. The process produced 99.6 grams of bromo-3,5-dimethoxytrifluoroacetanilide in 93% yield.

EXAMPLE 13

This example provides various conditions in accordance with the present invention for the conversion of 2-amino-4,6-dimethoxybenzonitrile to 2-amino-4,6-dimethoxybenzamide. The main routes for hydrating are: acidic, basic, and catalytic (involving a catalyst in addition to another reagent), or use of various groups of metals to facilitate the reaction. The reaction time varies. In the following conditions, the optimal reaction temperature range is from about 100° C. to about 115° C., with reaction completion in 1 hour to 2 hours.

2-amino-4,6-dimethoxybenzonitrile (2-amino-4,6-dimethoxybenzonitrile), $CH_3SO_3H$, with or without $Al_2O_3$, workup with KOH and/or 50% caustic and/or phosphate buffer and/or 30% potassium carbonate at 120° C. for 2-4 hours. Product not isolated. Conversion to 2-amino-4,6-dimethoxybenzamide: 78-88% (by HPLC).

2-amino-4,6-dimethoxybenzonitrile, $CH_3SO_3H$. Workup with 50% caustic; Precipitation in 1-4 DCM/1-6 MtBE at 120° C. for 0.5-4 hours. Isolated yield 28-64%; Purity 97.5-98.2% of 2-amino-4,6-dimethoxybenzamide;

2-amino-4,6-dimethoxybenzonitrile, $CH_3SO_3H$. Workup with 50% caustic; Precipitation in 1:3.2 DCM/MtBE at 120° C. for 1 hour. Isolated yield 78.5%; Purity 99.64% of 2-amino-4,6-dimethoxybenzamide.

2-amino-4,6-dimethoxybenzonitrile, $CH_3SO_3H$. Workup with 50% caustic; Precipitation in 1:3.2 DCM/MtBE at 100-115° C. for 1.5 hours. Isolated yield 75.7%; Purity 99.82% of 2-amino-4,6-dimethoxybenzamide.

2-amino-4,6-dimethoxybenzonitrile, $CH_3SO_3H$. Workup with 50% caustic; Precipitation in 1.6:1 Isopropyl acetate/MtBE at 105-110° C. for 2 hours. Isolated Yield 77.7%; Purity 99.58% of 2-amino-4,6-dimethoxybenzamide.

2-amino-4,6-dimethoxybenzonitrile, $CH_3SO_3H$. Workup with 50% caustic (no DCM-alternate solvent); Precipitation in 1.38:1 Isopropyl acetate/MtBE at 105-110° C. for 2 hours. Isolated Yield 77.1%; Purity 99.61% of 2-amino-4,6-dimethoxybenzamide 2-amino-4,6-dimethoxybenzonitrile, powdered 85% potassium hydroxide, t-butanol at 85° C. for 20.4 hours. Product not isolated. Conversion to 2-amino-4,6-dimethoxybenzamide 76% (by GC).

2-amino-4,6-dimethoxybenzonitrile, polyphosphoric acid at 115° C. for 6.9 hours. Product not isolated. Conversion to 2-amino-4,6-dimethoxybenzamide 100% (by GC).

2-amino-4,6-dimethoxybenzonitrile, 85% Sodium Hydroxide, 1,2-Propanediol, Water, Microwave at 150° C. for 0.16-58 hours. Product not isolated. Conversion to 2-amino-4,6-dimethoxybenzamide 60-84% (by GC).

2-amino-4,6-dimethoxybenzonitrile, 85% Potassium Hydroxide, t-Butanol, Microwave. 150° C. 0.08-1.08 hours. Product not isolated. Conversion to 2-amino-4,6-dimethoxybenzamide 62-84% (by GC).

2-amino-4,6-dimethoxybenzonitrile, $NaBO_3.H_2O$, MeOH, water at 50° C. for 48 hours. Product not isolated. Conversion to 2-amino-4,6-dimethoxybenzamide ~5% (by GC).

2-amino-4,6-dimethoxybenzonitrile, acetaldoxime, Pd-catalyst, $PPh_3$, aqueous ethanol at 75° C. for 22-144 hours. Product not isolated. Conversion to 2-amino-4,6-dimethoxybenzamide 20-36% (by GC).

2-amino-4,6-dimethoxybenzonitrile, acetaldoxime, Pd-catalyst, $PPh_3$, toluene at 75° C. for 144 hours. Product not isolated. Conversion to 2-amino-4,6-dimethoxybenzamide 12-18% (by GC).

2-amino-4,6-dimethoxybenzonitrile, KOH (flakes), t-amyl alcohol, $H_2O$, Lewis acid (cat.) at 98° C. for 22-130 hours. Product not isolated. Conversion to 2-amino-4,6-dimethoxybenzamide 9-49% (by GC).

2-amino-4,6-dimethoxybenzonitrile, Cesium or Barium hydroxide, t-Amyl Alcohol at 106° C. for 19-20 hours. Product not isolated. Conversion to 2-amino-4,6-dimethoxybenzamide ~2-3% (by GC).

2-amino-4,6-dimethoxybenzonitrile, Methanesulfonic Acid, Glacial Acetic Acid at 120° C. for 8.7 hours. Product not isolated. Conversion to 2-amino-4,6-dimethoxybenzamide 1.8% (by GC).

2-amino-4,6-dimethoxybenzonitrile, Ferric Nitrate*$9H_2O$, Water at 100° C. for 21 hours. Product not isolated. Conversion to 2-amino-4,6-dimethoxybenzamide 0.4% (by GC).

It is to be understood that the reactants and components referred to by chemical name or formula anywhere in this document, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical operation or reaction or in forming a mixture to be used in conducting a desired operation or reaction. Also, even though an embodiment may refer to substances, components and/or ingredients in the present tense ("is comprised of", "comprises", "is", etc.), the reference is to the substance, component or ingredient as it existed at the time just before it was first contacted, blended or mixed with one or more other substances, components and/or ingredients in accordance with the present disclosure.

Also, even though the claims may refer to substances in the present tense (e.g., "comprises", "is", etc.), the reference is to the substance as it exists at the time just before it is first contacted, blended or mixed with one or more other substances in accordance with the present disclosure.

Except as may be expressly otherwise indicated, the article "a" or "an" if and as used herein is not intended to limit, and should not be construed as limiting, the description or a claim to a single element to which the article refers. Rather, the article "a" or "an" if and as used herein is intended to cover one or more such elements, unless the text expressly indicates otherwise.

This invention is susceptible to considerable variation within the spirit and scope of the appended claims.

The invention claimed is:

1. A process for producing at least one (Compound I)

wherein the process comprises:
(i) combining at least one (Compound II)

with at least one halogenating agent to produce at least one (Compound III)

(ii) combining the at least one Compound III with at least one cyanating agent to produce at least one (Compound IV)

and;
(iii) combining the at least one Compound IV with at least one hydrating agent and/or at least one hydrating catalyst to produce the at least one Compound I,
wherein $R^1$ and $R^5$ each independently represent a hydrogen, a $C_1$-$C_6$ alkyl, a hydroxy, or a $C_1$-$C_6$ alkoxy;
wherein $R^2$, $R^3$, and $R^4$ each independently represent a hydrogen, a $C_1$-$C_6$ alkyl, or a $C_1$-$C_6$ alkoxy;
wherein $R^6$ and $R^7$ each independently represent a hydrogen, a $C_1$-$C_6$ alkyl, a protecting group, or a directing group;
wherein X represents a halo moiety or a halo-like moiety;
wherein at least one of $R^1$ and $R^5$ represent a hydrogen; and
provided that in Compound II, $R^7$ represents a protecting group or a directing group, and either
(1) prior to step (ii), the at least one Compound III is combined with at least one deprotecting agent such that the protecting group or directing group represented by $R^7$ is replaced with a hydrogen or a $C_1$-$C_6$ alkyl, or
(2) prior to step (iii), the at least one Compound IV is combined with at least one deprotecting agent such that the protecting group or directing group represented by $R^7$ is replaced with a hydrogen or a $C_1$-$C_6$ alkyl.

2. A process for producing at least one (Compound I)

wherein the process comprises:
(i) combining at least one (Compound II)

with at least one halogenating agent to produce at least one (Compound III)

(ii) combining the at least one Compound III with at least one cyanating agent to produce at least one (Compound IV)

(iii) combining the at least one Compound IV with at least one first precipitating agent to precipitate the at least Compound IV; and
(iv) combining the at least one Compound IV with at least one hydrating agent and/or at least one hydrating catalyst to produce the at least one Compound I,
wherein $R^1$ and $R^5$ each independently represent a hydrogen, a $C_1$-$C_6$ alkyl, a hydroxy, or a $C_1$-$C_6$ alkoxy;
wherein $R^2$, $R^3$, and $R^4$ each independently represent a hydrogen, a $C_1$-$C_6$ alkyl, or a $C_1$-$C_6$ alkoxy;
wherein $R^6$ and $R^7$ each independently represent a hydrogen, a $C_1$-$C_6$ alkyl, a protecting group, or a directing group;
wherein X represents a halo moiety or a halo-like moiety;
wherein at least one of $R^1$ and $R^5$ represent a hydrogen; and
provided that in Compound II, $R^7$ represents a protecting group or a directing group, and either
(1) prior to step (ii), the at least one Compound III is combined with at least one deprotecting agent such that the protecting group or directing group represented by $R^7$ is replaced with a hydrogen or a $C_1$-$C_6$ alkyl, or
(2) prior to step (iii), the at least one Compound IV is combined with at least one deprotecting agent such that the protecting group or directing group represented by $R^7$ is replaced with a hydrogen or a $C_1$-$C_6$ alkyl.

3. The process according to claim 2 wherein prior to step (iv), the at least one Compound IV is combined with at least one second precipitating agent to precipitate the at least one Compound IV.

4. The process according to claim 2 wherein prior to step (ii), the at least one Compound III is combined with at least one deprotecting agent such that the protecting group or directing group represented by $R^7$ is replaced with a hydrogen or a $C_1$-$C_6$ alkyl.

5. The process according to claim 2 wherein prior to step (iii), the at least one Compound IV is combined with at least one deprotecting agent such that the protecting group or directing group represented by $R^7$ is replaced with a hydrogen or a $C_1$-$C_6$ alkyl.

6. The process according to claim 2 wherein the at least one Compound II is produced by a process comprising combining at least one (Compound V)

with at least one protecting agent to produce the at least one Compound II,
wherein $R^{6'}$ and $R^{7'}$ each independently represent a hydrogen or a $C_1$-$C_6$ alkyl.

7. The process according to claim 2 wherein X represents Cl, Br, I, -OTf, -OMs, or -OTs.

8. The process according to claim 2 wherein at least one of $R^1$, $R^2$, $R^3$, $R^4$, or $R^5$ represents a $C_1$-$C_6$ alkoxy.

9. The process according to claim 2 wherein at least two of $R^1$, $R^2$, $R^3$, $R^4$, and $R^5$ each independently represent a $C_1$-$C_6$ alkoxy.

10. The process according to claim 2 wherein at least three of $R^1$, $R^2$, $R^3$, $R^4$, and $R^5$ each independently represent a $C_1$-$C_6$ alkoxy.

11. The process according to claim 2 wherein $R^2$ and $R^4$ each independently represent a $C_1$-$C_6$ alkoxy, and $R^1$ and $R^3$ each represent a hydrogen.

12. The process according to claim 11 wherein the $C_1$-$C_6$ alkoxy is a methoxy.

13. The process according to claim 6, wherein the protecting agent comprises an anhydride.

14. The process according to claim 13, wherein the anhydride is trifluoroacetic anhydride.

15. The process according claim 2, wherein the at least one halogenating agent comprises DBDMH.

16. The process according to claim 2, wherein the hydrating agent comprises water.

17. The process according to claim 2, wherein the hydrating catalyst comprises at least one acid.

18. The process according to claim 17, wherein the at least one acid is selected from trifluoroacetic, sulfuric and methanesulfonic acid.

19. The process according to claim 2, further comprising conducting steps (i)-(iii) in a one-pot process reaction.

20. The process according to claim 2, wherein in Compound II, $R^2$ and $R^4$ each independently represent a $C_1$-$C_6$ alkoxy, $R^1$ and $R^3$ each represent a hydrogen, and $R^7$ represents trifluoroacetyl.

21. The process according to claim 2, wherein the at least one halogenating agent comprises N-bromosuccinimide.

22. The process according to claim 2, wherein the at least one cyanating agent comprises CuCN.

23. The process according to claim 2, wherein the at least one cyanating agent comprises $K_4Fe(CN)_6$ and CuI.

24. The process according to claim 2, wherein Compound I is 2-amino-4,6-dimethoxybenzamide.

25. A process comprising:
(i) protecting 3,5-dimethoxyaniline with a protecting agent to produce a protected 3,5-dimethoxyaniline;
(ii) halogenating the protected 3,5-dimethoxyaniline with a halogenating agent to produce a halogenated protected 3,5-dimethoxyaniline;
(iii) cyanating the halogenated protected 3,5-dimethoxyaniline with a cyanating agent to produce a cyanated protected 3,5-dimethoxyaniline;
(iv) deprotecting the cyanated protected 3,5-dimethoxyaniline; and
(v) hydrating the precipitate comprising the cyanated 3,5-dimethoxyaniline to produce 2-amino-4,6-dimethoxybenzamide.

26. A process comprising:
(i) protecting 3,5-dimethoxyaniline with a protecting agent to produce a protected 3,5-dimethoxyaniline;
(ii) halogenating the protected 3,5-dimethoxyaniline with a halogenating agent to produce a halogenated protected 3,5-dimethoxyaniline;
(iii) cyanating the halogenated protected 3,5-dimethoxyaniline with a cyanating agent to produce a cyanated protected 3,5-dimethoxyaniline;
(iv) deprotecting the cyanated protected 3,5-dimethoxyaniline and inducing precipitation to produce a precipitate comprising the cyanated 3,5-dimethoxyaniline; and
(v) hydrating the precipitate comprising the cyanated 3,5-dimethoxyaniline to produce 2-amino-4,6-dimethoxybenzamide.

27. A process comprising:
(i) protecting 3,5-dimethoxyaniline with a protecting agent to produce a protected 3,5-dimethoxyaniline;
(ii) halogenating the protected 3,5-dimethoxyaniline with a halogenating agent to produce a halogenated protected 3,5-dimethoxyaniline;
(iii) cyanating the halogenated protected 3,5-dimethoxyaniline with a cyanating agent to produce a cyanated protected 3,5-dimethoxyaniline;
(iv) deprotecting the cyanated protected 3,5-dimethoxyaniline and inducing precipitation to produce a first precipitate comprising the cyanated 3,5-dimethoxyaniline;
(v) re-precipitating the first precipitate comprising the cyanated 3,5-dimethoxyaniline to produce a second precipitate comprising the cyanated 3,5-dimethoxyaniline; and
(vi) hydrating the second precipitate comprising the cyanated 3,5-dimethoxyaniline to produce 2-amino-4,6-dimethoxybenzamide.

28. A process comprising:
(i) protecting a 3,5-dimethoxyaniline with a protecting agent to produce a protected 3,5-dimethoxyaniline;
(ii) halogenating the protected 3,5-dimethoxyaniline with a halogenating agent to produce a halogenated protected 3,5-dimethoxyaniline;
(iii) deprotecting the halogenated protected 3,5-dimethoxyaniline to produce a halogenated 3,5-dimethoxyaniline;
(iv) precipitating the halogenated 3,5-dimethoxyaniline;
(v) cyanating the halogenated 3,5-dimethoxyaniline with a cyanating agent to produce a cyanated 3,5-dimethoxyaniline;
(vi) precipitating the cyanated 3,5-dimethoxyaniline, and
(vii) hydrating the precipitated cyanated 3,5-dimethoxyaniline to produce 2-amino-4,6-dimethoxybenzamide.

29. The process according to claim 27 or claim 28, wherein the protected 3,5-dimethoxyaniline is 3,5-dimethoxytrifluoroacetanilide.

30. The process according to claim 27 or claim 28, wherein the halogenated protected 3,5-dimethoxyaniline comprises bromo-3,5-dimethoxytrifluoroacetanilide isomers.

31. The process according to claim 27 or claim 28, wherein the cyanated protected 3,5-dimethoxyaniline comprises cyano-3,5-dimethoxytrifluoroacetanilide isomers.

32. The process according to claim 27 or claim 28, wherein the protecting agent comprises an anhydride.

33. The process according to claim 32, wherein the anhydride is trifluoroacetic anhydride.

34. The process according to claim 27 or claim 28, wherein the protecting agent is an acid chloride.

35. The process according to claim 27 or claim 28, wherein the halogenating agent comprises N-bromosuccinimide.

36. The process according to claim 27 or claim 28, wherein the cyanating agent comprises CuCN.

37. The process according to claim 27 or claim 28, wherein the cyanating agent comprises $K_4Fe(CN)_6$ and CuI.

38. The process according to claim 27 or claim 28, wherein the hydrating agent comprises water.

39. The process according claim 27 or claim 28, wherein the hydrating catalyst comprises at least one acid selected from trifluoroacetic acid, sulfuric acid, and methanesulfonic acid.

* * * * *